(12) United States Patent
Davis

(10) Patent No.: US 10,137,215 B2
(45) Date of Patent: Nov. 27, 2018

(54) ORGANIC WASTE ODOR ABSORBER

(71) Applicant: Shawn Sumeet Davis, Surrey (CA)

(72) Inventor: Shawn Sumeet Davis, Surrey (CA)

(*) Notice: Subject to any disclaimer, the term of this patent is extended or adjusted under 35 U.S.C. 154(b) by 0 days.

(21) Appl. No.: 15/406,775

(22) Filed: Jan. 15, 2017

(65) Prior Publication Data

US 2017/0165388 A1 Jun. 15, 2017

Related U.S. Application Data

(62) Division of application No. 14/737,494, filed on Jun. 12, 2015.

(60) Provisional application No. 62/010,458, filed on Jun. 11, 2014.

(51) Int. Cl.
A61L 9/014 (2006.01)
A61L 9/012 (2006.01)
A61L 9/013 (2006.01)
B01J 20/24 (2006.01)
B01J 20/10 (2006.01)

(52) U.S. Cl.
CPC ............... *A61L 9/014* (2013.01); *A61L 9/012* (2013.01); *A61L 9/013* (2013.01); *B01J 20/103* (2013.01); *B01J 20/24* (2013.01); *A61L 2209/21* (2013.01); *A61L 2209/22* (2013.01)

(58) Field of Classification Search
CPC .................................. A61L 9/014; A61L 9/013
See application file for complete search history.

(56) References Cited

FOREIGN PATENT DOCUMENTS

GB          2439047 A  * 12/2007  ............... A61L 9/01

* cited by examiner

*Primary Examiner* — Nicole P Babson

(57) ABSTRACT

An organic waste odor absorbing composition for the absorption of odors resulting from decomposing organic waste is disclosed. The composition comprises dried carbon and/or silica based matter, either natural or synthetic. The carbon-based materials consist of 35% to 85% holocellulose and 8% to 30% lignin. The silica-based materials consist of 40% to 80% silica. The materials may be mechanically sized to allow for adequate airflow and surface area exposure to the organic waste.

3 Claims, No Drawings

ORGANIC WASTE ODOR ABSORBER

CROSS REFERENCE TO RELATED APPLICATION

The present application claims benefit of Provisional Application No. 62/010,458 filed Jun. 11, 2014, entitled "Organic Waste Odor Absorber". The Provisional Application and the patent are incorporated herein by reference, including their specifications. It should be noted that the referenced Provisional Application is not admitted to be prior art with respect to the present invention by its mention in the background or cross-reference section.

This is a divisional of patent application Ser. No. 14/737,494.

1.0—BACKGROUND

'Organic waste' can be described as anything that comes from plants or animals that is biodegradable. The term 'waste' implies that the organic matter from a plant or animal was not used for its intended purpose, or is 'leftover'. For example, after a chicken is cooked and eaten, the bones of the skeleton are leftover and cannot be ingested any further by most humans. Thus, the remaining bones have become organic waste, and will be disposed of. Furthermore, organic waste can include paper products, such as paper napkins or paper towels, derived from plant materials. Other examples of organic waste include vegetable scraps, fruit scraps, cut grass, coffee grounds, milk, and newspaper.

Organic waste that is produced by urban establishments, including households, offices, libraries, restaurants, and schools, can be used to produce compost. Compost is organic waste that has been decomposed by living microorganisms to be used as a fertilizer for soil. These microorganisms gain energy from the carbon found in the organic waste, and use the nitrogen in the organic waste to grow and reproduce.

Thus, healthy compost has a carbon/nitrogen (C/N) ratio that aids these microorganisms. Furthermore, air plays a vital role in the breakdown by microorganisms of carbon for their energy, and lack of air can produce a rotten egg like smell that emanates from the organic waste pile. For proper decomposition of organic waste, air and its constituent elements, i.e., oxygen, nitrogen, carbon dioxide, etc., must contact the organic waste. It is also necessary to control moisture levels in the compost. Too much moisture in the processes leading up to the final compost product are signs of an unbalanced, and thus an unhealthy, compost. Excess moisture is also a key contributor to harsh odors. It is necessary to control moisture levels throughout the compost creation process.

To reduce or eliminate such odours is desirable for many reasons. When organic waste is left to decompose in close proximity to human habitats i.e., offices, apartments, houses, lobbies, etc., odors can create undesirable atmospheres that may limit normal human activity. Furthermore, the unpleasant odors can deter humans from partaking in the duty of separating and removing organic waste in the most efficient and environmentally friendly manner. Thus, organic waste is not separated and is disposed of with normal waste or garbage to the landfill, bypassing infrastructure and technology intended to dispose of organic waste separately.

This inefficient allocation of organic waste results in adverse environmental and economic effects. For instance, many communities have implemented organic waste disposal programs, which redirect organic waste from the landfill to facilities that specialize in the recycling of organic waste. Each member of such a community is given a method of which to dispose of their organic waste. If members do not partake in this program, there are two general adverse effects: First, the resources allotted to the program are either not utilized or are under utilized, resulting in an inefficient allocation of the resources. Second, organic waste is disposed of in traditional disposal sites, which increase the size of these sites, and also forgoes organic wastes' ability to be recycled into compost, fertilizer, energy, feed stock, etc., resulting in environmentally adverse impacts.

Information relevant to attempts to address these problems can be found in: Canadian Patent Numbers 2770305, 2234198, 2226022, 1218320, 2226022, 1260728, and 1222640. German Patent Number 19534874. Russian Patent Number 0002414444. Australian Patent Number 202247. World Patent Number 2002013949. However, each one of these references suffers from one or more of the following disadvantages:

There is a masking of smell, rather than a removal of the smell. This is exhibited when inventions utilize pleasant smelling fragrances without manipulating the chemical reactions within the organic waste that produce malodorous substances. This masking effect may remedy the initial malodorous substances produced when organic waste is first disposed of in a receptacle near humans, i.e., homes, apartments, offices, libraries, etc., however, when this organic waste is transported to secondary storage areas from the initial receptacle, the smell is still prevalent. One instance of this could occur in an apartment building where organic waste must be transported from individual apartment units to a collective disposal area to wait for removal to a treatment facility. Organic waste will continue to decompose and produce unpleasant odors.

Another problem associated with one or more of these references is the inability to economically translate the embodiments to various receptacles that hold organic waste. Various receptacles are used in the storage and transportation of organic waste from initial disposal to final recycling, each with different dimensions and or functionalities. The possible difference in receptacles present a problem for previous inventions that can not form to the dimensions or functionalities of these receptacles, thus hindering the ability to reduce malodors from the organic waste.

Another problem associated with one or more of these references is the lack of aeration provided to the core of the organic waste pile. In other words, lack of air is present in areas in the middle of the organic waste pile, thus producing malodors. It is not enough to simply provide aeration to the top of an organic waste pile because lack of aeration in the lower levels of the organic waste pile are sites where malodors will be produced. Furthermore, additives to the organic waste heap may cause clumping or congestion, which can also reduce airflow to parts of the organic waste pile.

For the forging reasons, there is a need for a carbon-based odor absorbent for organic waste that works with the natural chemistry of the waste, provides efficient air flow to the waste, and is economically viable to produce and use in today's society.

2.0—SUMMARY

The present invention is directed to an organic waste odor absorbing composition that satisfies these needs (needs identified in the Background section). The organic waste odor absorbing composition comprises one or more materials that are derived from dried, carbon and/or silica based matter that is produced by natural or synthetic means. The matter itself may be mechanically sized to allow for adequate airflow and surface area exposure when added to the organic waste. It is not necessary to mechanically size the matter if it is already of optimal size after harvest or production. It is also optional to add natural or synthetic scents to the matter to further reduce harsh odors originating from the organic waste.

3.0—DESCRIPTION

In the Summary above and in the Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, materials, etc. are optionally present. For example, an article "comprising" (or "which comprises") components A, B, and C can consist of (i.e., contain only,) components A, B, and C, or can contain not only components A, B, and C but also one or more other components.

The usage of '(s)' after a root word used herein means that one or more of the root word may be used. For example, 'nail(s)' means that there could be one nail present, two nails present, or ten nails present.

The term "at least" followed by a number is used herein to denote the start of a range beginning with that number, which may be a range having an upper limit or no upper limit, depending on the variable being defined. For example, "at least 1" means 1 or more than 1. The term "at most" followed by a number is used herein to denote the end of a range ending with that number, which may be a range having 1 or 0 as its lower limit, or a range having no lower limit, depending upon the variable be defined. For example, "at most 4" means 4 or less than 4, and "at most 40%" means 40% or less than 40%. When, in this specification, a range is given as "(a first number) to (a second number)", this means a range whose lower limit is the first number and whose upper limit is the second number. For example, 25 to 100 mm means a range whose lower limit is 25 mm, and whose upper limit is 100 mm.

Listed here are definitions to be used for clarification:

"Organic waste" is a type of waste that comes from plants or animals, and is broken down in a reasonable time, into its base compounds.

"Compost" is organic waste that has been thoroughly decomposed and recycled as a soil amendment.

"Waste" is organic matter from a plant or animal that is not used for its intended purpose, or is 'leftover'.

"Receptacle" is an object or space used to contain something.

"Combination" is various components described working together, usually in reference to one or more components.

"Plant" is a multi-celled organism of the kingdom Plantae.

"Kingdom" is a taxonomic rank.

"Holocellulose" is the total polysaccharide fraction of wood or straw and the like that is made up of cellulose and all of the hemicelluloses and that is obtained by removing the extractives and the lignin from the original natural material.

The organic waste odor absorbing composition comprises one or more materials that interact to reduce odors that originate from organic waste as it continues to decompose. The matter that makes up the material(s) comprises dried carbon and/or dried silica based matter from natural or synthetic sources. It is necessary that the composition comprise dried material(s) as this will promote moisture absorption.

The composition is able to reduce the odors that are emitted from organic waste. This is achieved essentially by balancing the carbon to nitrogen content, when the composition is added to the organic waste. The carbon content found within the composition mixes with the high nitrogen content of the organic waste, providing the energy to microorganisms to decompose the organic waste and the composition itself. Thus, transferring the optimal amount of carbon to these microorganisms is vital in reducing odors resulting from excess nitrogen that results from a lack of carbon.

The composition may also be derived from natural or synthetic material(s), meaning that the material(s) can come from natural occurring matter or be produced synthetically. An example of a natural occurring matter to be used as a material in the composition could be clay removed from clay deposits found on the earth. Another example could be the remains of crops, in particular, the dried stalks or leaves of the crop. An example of synthetically produced matter to be used as a material in the composition could be a crystalline powder that is primarily carbon and/or silica based that is produced in via synthetic means.

Ideally, the carbon-based material(s) will contain between 35% to 85% holocellulose and between 8% to 30% lignin content (as a percent by dry weight) to promote quick breakdown of the material(s) when added to the nitrogen-rich organic waste. Testing the content of holocellulose and lignin can be achieved by many known in the related art scientific methods. In particular, one could determine the contents of lignin via spectrophotometric determination. Holocellulose content can be determined using the sodium chlorite micromethod. For example, research has shown that the trembling aspen (*Populus tremuloides*) is comprised of 19% lignin and 78% holocellulose. Furthermore, any type of plant material that is chosen should removed of all possible infestations of insects or external agents that can cause contamination to end product.

Ideally, the silica-based materials will contain approximately 40% to 80% silica. This can be measured via infrared spectroscopy.

The chosen matter to make up one or more materials in the organic waste odor absorbing composition may need to be sized mechanically if it is not already of the optimal dimensions after harvest or production. This mechanical sizing can occur via chopping, cutting, 3D printing, etc. The optimal sizing of the materials will depend on the type of organic waste and the size of the receptacle in which the organic waste is stored. Furthermore, either if one or more materials is chosen, different sizing of the material or materials may be necessary to provide adequate airflow and surface area exposure. For example, within the combination of plant materials used in the composition, A+B: A can be finely ground up into a dust like material that exposes a large amount of surface area. B can be less ground, producing less surface area, yet its larger frame allows for more space in between B type chunks and other particles, and thus more space for aeration.

Ideally, for an organic waste receptacle measuring approximately 729 cubic inches, the materials used in the composition should measure from small particles at least 0.002 mm to 10 mm (according to ISO 14688-1) to larger pieces that can range in size from approximately 2 mm by 2 mm by 2 mm (Length by Width by Height) to approximately 15 mm by 15 mm by 15 mm. It should be noted that these ranges do not mean that the pieces must be squares, but can include varying dimensions of length, width, and height. For example, the above ranges for pieces can include pieces that are 3 mm by 8 mm by 10 mm.

Ideally, for an organic waste receptacle measuring approximately 2 cubic yards, the materials used in the composition should measure from small particles approximately 0.002 mm to 10 mm (according to ISO 14688-1) to larger pieces that can range in size from approximately 2 mm by 2 mm by 2 mm (Length by Width by Height) to approximately 300 mm by 300 mm by 300 mm. It should be noted that these ranges do not mean that the pieces must be squares, but can include varying dimensions of length, width, and height. For example, the above ranges for pieces can include pieces that are 3 mm by 70 mm by 250 mm.

The minimum and maximum particle and piece sizes should be chosen based on the size of the receptacle and the bin size.

The chosen matter can then be sprayed with natural or synthetic scents derived from various species of plants. For example, one can derive scents from the oils of a cedar tree, or from a eucalyptus plant, and then may dilute the oils and spray them or soak them into the chosen matter for the composition. Such scenting can further promote the odor reducing qualities of the composition.

The organic waste odor absorbing composition can first be placed on the bottom of a receptacle before any organic waste is added. This will create a layer unto which moisture from the organic waste, and the organic waste itself can mix with the composition. The amount of composition added to the bottom of the receptacle depends on the amount of organic waste, moisture content of the organic waste, and the size of the receptacle. As organic waste is added, more of the composition should be added at select intervals, once again dependent on the amount of organic waste and its moisture content. The optimal ratio of the composition to organic waste will reduce the most amount of odor. Through minimal trial and error, users of the composition can determine what amount of composition is optimal for the organic waste they produce and recycle.

The composition can also be used with a receptacle that utilizes bags to hold the organic waste, thus making cleaning of the receptacle easier. The composition is placed in the receptacle, under the bag. Organic waste that is added to the bag and causes tears in the bag may result in moisture leaking to down into the composition. The composition absorbs this excess moisture, reducing cleaning frequencies and odors.

3.1—EXAMPLES

Example 1

This example shows a formulation of the composition. Two materials are used to make the final composition, a single plant material, *Cannabis Sativa* L., with a holocellulose content of 78% and a lignin content of 18% (% by dry weight), and clay, with a silica content of approximately 70%. The plant is dried, and the inner stalk is separated from the outer fibers and chipped down via a motorized chipper. The average size of the resulting particles are 15 cubic millimeters. The clay has a particle size of 0.005 millimeters according to the ISO 14688-1. The clay did not need to be mechanically sized, as this is its natural form. Both materials are mixed together and a light cedarwood scent is added by mixing cedarwood essential oils with materials.

Example 2

This example shows how the material is used at a commercial establishment. The composition is added to a clean organic waste receptacle, a 2 cubic yard dumpster. A layer approximately 1 inch deep is added to the bottom of the entire dumpster. Throughout the week of business, tenants place their organic waste into the dumpster, on top of the composition. Janitors also add more composition throughout the week to further reduce the smell of the decomposing organic waste. The dumpster is then emptied by the waste management contractor. After it is emptied, more of the composition is added to prepare for the organic waste for next week.

While the invention has been specifically described in connection with certain specific embodiments thereof, it is to be understood that this is by way of illustration and not of limitation, and the scope of the appended claims should be construed as broadly as the prior art will permit.

The reader's attention is directed to all papers and documents which are filed concurrently with this specification and which are open to public inspection with this specification, and the contents of all such papers and documents are incorporated herein by reference.

What is claimed is:

1. A method of treating organic waste comprising:
 a step of placing a composition within a receptacle to create a layer on the bottom of said receptacle;
 a step of placing organic waste within said receptacle already containing the layer of said composition, where said organic waste is placed on top of said composition;
 a step of placing additional said composition on top of said organic waste within said receptacle;
 wherein said composition's materials comprise:
  a. 35% to 85% holocellulose, by weight
  b. 8% to 30% lignin, by weight
  c. 40% to 80% silica, by weight;
 wherein said composition comprises dried materials;
 wherein said composition's materials comprise a particle size range from 0.002 millimeters in diameter to 300 by 300 by 300 millimeters;
 wherein said composition comprises a scent;
 wherein said organic waste is composted.

2. The method of claim 1, wherein the receptacle comprises a receptacle that is designed to hold organic waste.

3. The method of claim 1, wherein the composition comprises a scent consisting of a natural or synthetic oil extract.

\* \* \* \* \*